(12) United States Patent
Rock et al.

(10) Patent No.: US 11,892,431 B2
(45) Date of Patent: Feb. 6, 2024

(54) ACOUSTIC ARRAY DETECTION AND IMAGING

(71) Applicant: ThunderTech Inc., Englewood, CO (US)

(72) Inventors: Alan Rock, Morrison, CO (US); Longpeng Zhang, Englewood, CO (US); Fangwei Han, Beijing (CN)

(73) Assignee: ThunderTech Inc., Englewood, CO (US)

( * ) Notice: Subject to any disclaimer, the term of this patent is extended or adjusted under 35 U.S.C. 154(b) by 40 days.

(21) Appl. No.: 17/162,551

(22) Filed: Jan. 29, 2021

(65) Prior Publication Data

US 2021/0302389 A1 Sep. 30, 2021

Related U.S. Application Data

(60) Provisional application No. 63/002,874, filed on Mar. 31, 2020.

(51) Int. Cl.
*G01N 29/26* (2006.01)
*A61B 8/00* (2006.01)
*G01N 29/06* (2006.01)

(52) U.S. Cl.
CPC ......... *G01N 29/262* (2013.01); *A61B 8/4488* (2013.01); *A61B 8/54* (2013.01); *G01N 29/0681* (2013.01); *G01N 2291/106* (2013.01)

(58) Field of Classification Search
CPC ............ G01N 29/262; G01N 2291/106; A61B 8/4488; A61B 8/54
See application file for complete search history.

(56) References Cited

U.S. PATENT DOCUMENTS

| 2001/0020131 A1* | 9/2001 | Kawagishi | G10K 11/346 600/443 |
| 2012/0330569 A1* | 12/2012 | Singh | G01N 29/069 702/39 |
| 2018/0368807 A1* | 12/2018 | Van De Pas | A61B 8/4254 |

* cited by examiner

*Primary Examiner* — Isam A Alsomiri
*Assistant Examiner* — Abdallah Abulaban
(74) *Attorney, Agent, or Firm* — King Intellectual Asset Management

(57) ABSTRACT

Novel tools and techniques for acoustic array detection and imaging are provided. A system includes an acoustic array comprising one or more array panels. Each of the one or more array panels includes a transceiver array of one or more acoustic transceivers, each acoustic transceiver further including a transmitter element configured to generate sound and a receiver element to capture sound. A driver circuit is coupled to a first transceiver array of a first array panel of the one or more array panels, the driver circuit configured to drive individually each transmitter element and each receiver element of the first transceiver array. A controller interface is coupled to the driver circuit, and a controller coupled to the controller interface.

21 Claims, 10 Drawing Sheets

ACOUSTIC ARRAY DETECTION AND IMAGING

CROSS REFERENCE TO RELATED APPLICATIONS

This application claims priority to U.S. Provisional patent Application Ser. No. 63/002,874, filed Mar. 31, 2020 by Alan Rock et al., entitled "Acoustic Array Detection and Imaging," the entire disclosure of which is incorporated herein by reference in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to acoustic detection and imaging techniques, and more particularly to a novel acoustic array and algorithm for improved acoustic detection and imaging.

BACKGROUND

Ultrasound and other sonographic techniques have traditionally been used for non-invasive medical imaging, non-destructive testing, detection, and ranging applications. Conventional ultrasound techniques employ single-element probes (e.g., monolithic probes) comprising a single ultrasonic transducer or a single ultrasonic transmitter and receiver pair, and alternatively, ultrasonic transducer arrays comprising two or more ultrasonic transducers or ultrasonic transmitter and receiver pairs positioned in a linear arrangement.

Traditional acoustic microscopy typically relies on a single ultrasound transducer that is two-dimensionally scanned over a specimen. Visualization using conventional techniques makes real-time imaging impractical. Time is required to scan the specimen, as well as processing time to complete imaging of the specimen. In traditional medical imaging and ultrasonic testing applications in which real-time images can be acquired, feature size and resolution are typically limited, and rely on technician manipulation and/or positioning of a transducer probe. Moreover, acoustic couplant (e.g., an ultrasound gel) may further be applied to aid in the coupling of the sonic signal from the transducer into the test medium.

Accordingly, tools and techniques for an acoustic array detection and imaging are provided below.

BRIEF DESCRIPTION OF THE DRAWINGS

A further understanding of the nature and advantages of the embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Figure 1:
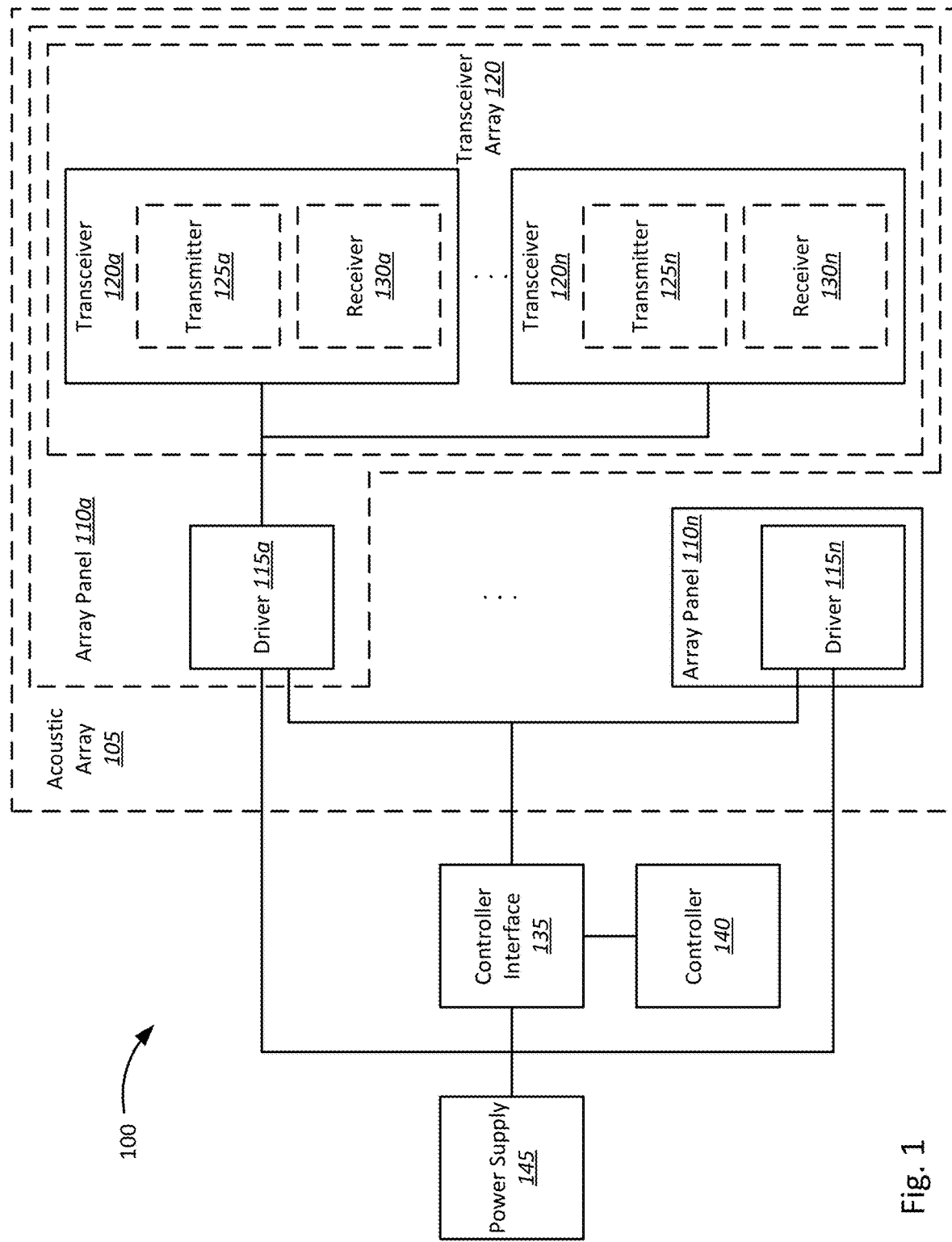
FIG. 1 is a schematic block diagram of a system for implementing acoustic array detection and imaging, in accordance with various embodiments.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The various embodiments include, without limitation, methods, systems, apparatuses, and/or software products. Merely by way of example, a method might comprise one or more procedures, any or all of which may be executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible, and/or non-transitory computer readable media (such as, to name but a few examples, optical media, magnetic media, and/or the like).

In one aspect, a system for acoustic array detection and imaging are provided. The system includes and acoustic array, driver circuit, controller interface, and controller. The acoustic array may include one or more array panels, each of the one or more array panels including a transceiver array of one or more acoustic transceivers, each acoustic transceiver further including a transmitter element configured to generate sound and a receiver element to capture sound. The driver circuit may be coupled to a first transceiver array of a first array panel of the one or more array panels, the driver circuit configured to drive individually each transmitter element and each receiver element of the first transceiver array. The controller interface may be coupled to the driver circuit. The controller may be coupled to the controller interface, the controller further including a processor, and non-transitory computer readable media comprising instructions executable by the processor to perform various functions. The instructions may include instructions to provide, via the controller interface, a probe signal to the driver circuit, provide, via the controller interface, a transmit focal point for the probe signal to be transmitted by the first transceiver array, adjust, via the driver circuit, a first phase of the probe signal at one or more transmitter elements of the first transceiver array based on the focal point, and emit, via the first transceiver array, the probe signal at the focal point.

In another aspect, an apparatus for acoustic array detection and imaging are provided. The apparatus includes a processor and non-transitory computer readable media comprising instructions executable by the processor to perform various functions. The instructions include instructions to provide a probe signal to a driver circuit of an acoustic array, the acoustic array comprising one or more array panels including a first array panel, each of the one or more array panels including a respective transceiver array, the first array panel comprising a first transceiver array, each transceiver array comprising one or more transceivers, each transceiver comprising a respective transmitter element and a respective receiver element, wherein the driver circuit is coupled to the first transceiver array, provide a transmit focal point for the probe signal to be transmitted by the first transceiver array, adjust, via the driver circuit of the first transceiver array, a first phase of the probe signal at one or more transmitter elements of the first transceiver array based on the focal point, and emit, via the first transceiver array, the probe signal at the focal point.

In a further aspect, a method for acoustic array detection and imaging are provided. The method includes providing, via a controller interface, a probe signal to a driver circuit of an acoustic array, the acoustic array comprising one or more array panels including a first array panel, each of the one or more array panels including a respective transceiver array, the first array panel comprising a first transceiver array, each transceiver array comprising one or more transceivers, each transceiver comprising a respective transmitter element and a respective receiver element, wherein the driver circuit is coupled to the first transceiver array. The method continues by providing, via the controller interface, a transmit focal point for the probe signal to be transmitted by the first transceiver array, and adjusting, via the driver circuit, a first phase of the probe signal at one or more transmitter elements of the first transceiver array based on the focal point. The method further includes emitting, via the first transceiver array, the probe signal at the focal point.

FIG. 1 is a schematic block diagram of a system 100 for implementing acoustic array detection and imaging, in accordance with various embodiments. The system 100 includes an acoustic array 105, one or more array panels 110a-110n (collectively "array panels 110") including a first array panel 110a through an nth array panel 110n, respective one or more driver circuits 115a-115n (collectively "driver circuits 115") including a first driver circuit 115a through an nth driver circuit 115n, a respective first transceiver array 120 including a first transceiver 120a through an nth transceiver 120n, respective transmitters 125a-125n including a first transmitter 125a through an nth transmitter 125n, respective receivers 130a-130n including a first receiver 130a through an nth receiver 130n, controller interface 135, controller 140, and power supply 145. It should be noted that the various components of the system 100 are schematically illustrated in FIG. 1, and that modifications to the system 100 may be possible in accordance with various embodiments.

In various embodiments, the acoustic array 105 may be coupled to a controller interface 135. The controller interface 135 may couple the controller 140 to the acoustic array 105. The power supply 145 may further be coupled to the acoustic array 105 via the controller interface 135. The acoustic array 105 may include one or more array panels 110a-110n. Each of the array panels 110 may include a respective driver circuit 115a-115n, and respective transceiver array 120. Each transceiver array 120 may include one or more transceivers 120a-120n. Each of the one or more transceivers 120a-120n may include a respective transmitters 125a-125n, and respective receiver 130a-130n. For example, the first array panel 110a includes a first driver circuit 115a, and a first transceiver array 120. The first transceiver 120 includes one or more transceivers 120a-120n. In some embodiments, the first transceiver 120a may include a first transmitter 125a and first receiver 130a. The nth transceiver 120n may include an nth transmitter 125n and an nth receiver 130n.

In various embodiments, the acoustic array 105 may include one or more array panels 110a-110n. In some embodiments, the one or more array panels 110a-110n may be a substantially flat structure having a polygonal, circular, elliptical, or alternatively, an irregularly shaped face/surface. For example, in some embodiments, the one or more array panels 110a-110n may be a square-shaped, rectangular-shaped, hexagonal-shaped, triangular-shaped, or other polygonal-shaped panel. In other embodiments, the one or more array panels 110a-110n may have an irregular shape configured for specific size or fitment constraints of a particular application.

In some embodiments, the one or more array panels 110a-110n may each have the same shape and/or size. In other embodiments, the one or more array panels 110a-110n may have different shapes and/or sizes. In yet further embodiments, a set of the one or more array panels 110a-110n may have a first shape and/or size, while another set of the one or more array panels 110a-110n may have a second shape and/or size different from the first shape and/or size. Accordingly, the one or more array panels 110a-110n may further comprise one or more sets of panels of varying shape and/or size.

The one or more array panels 110a-110n may be arranged in various configurations. In some embodiments, the one or more array panels 110a-110n may be arranged in a polyhedral arrangement, the one or more array panels 110a-110n defining faces of the polyhedron. For example, the acoustic array 105 may be a cube comprising six square array panels 110. In other embodiments, the one or more array panels 110a-110n may be positioned in a distributed arrangement. For example, the one or more array panels 110a-110n may be placed around a room, on a wall, or other distributed arrangement. In other examples, the one or more array panels 110a-110n may be placed such that they are not in physical contact with each other panel, or so that no array panels are within a threshold proximity from the closest point of an array panel to the closest point of another array panel.

In various embodiments, each of the one or more array panels 110a-110n may further comprise a respective transceiver array 120. A transceiver array 120 may be an array of one or more transceivers 120a-120n, arranged on at least one surface of a respective array panel. For example, in some embodiments, the transceiver array 120 may be arranged on a front surface, back surface, or along an edge of a respective array panel. In various embodiments, the transceiver array 120 may be arranged according to a specific pattern or shape. For example, in some embodiments, the one or more transceivers 120a-120n may be arranged into a two-dimensional array. In some examples, the one or more transceivers 120a-120n may be arranged into a square-shaped two-dimensional array. In other embodiments, the one or more transceivers 120a-120n may be arranged into different shapes, such as a rectangle, triangle, or other polygonal shape, or in a circular or elliptical shape. In some embodiments, the one or more transceivers 120a-120n may be arranged in an irregular pattern. In some further embodiments, the one or more transceivers 120a-120n may be arranged in a linear array, or as a plurality of linear arrays.

In various embodiments, each of the one or more transceivers 120a-120n may be distributed equally across the transceiver array 120. For example, each transceiver of the one or more transceivers 120a-120n may be spaced the same distance from a neighboring transceiver. In one example, the transceiver array 120 may be a square-shaped, two-dimensional 13×13 array of transceivers 120a-120n. Thus, the transceiver array 120 may comprise 13 rows of 13 transceivers. Each transceiver may be equally spaced from a neighboring transceiver, except for the first row, last row, first transceiver in each row, and last transceiver in each row. Thus, a given transceiver may be spaced an equal distance from a transceiver to its left, right, top, and bottom. As will be evident, in such an arrangement, each of the first transceivers of each row do not have a transceiver located to its left. Similarly, each of the last transceivers of each row do not have a transceiver located to its right. Each of the top row of transceivers do not have a transceiver above it, and each of the bottom row of transceivers do not have a transceiver located below it.

In some further embodiments, each of the one or more transceivers 120a-120n may be spaced irregularly, or according to a pattern. For example, in some embodiments, the transceiver array 120 may be relatively more densely populated with transceivers towards the center of the transceiver array 120 and relatively less densely populated by transceivers further away from the center of the transceiver array 120. In yet further embodiments, each transceiver array 120 may include two or more sub-arrays of one or more transceivers 120a-120n.

In various embodiments, the one or more transceivers 120a-120n may each comprise a respective transmitter 125a-125n, and respective receiver 130a-130n. The respective transmitters 125a-125n may include suitable acoustic transmitters. Thus, transmitters 125a-125n may include, without limitation, speakers, projectors, diaphragms, acoustic vibrating element, or other suitable transducer configured to generate sound. Receivers 130a-130n may include suitable acoustic receivers including, without limitation, a microphone or other suitable transducer configured to receive and detect sound (e.g., convert sound into an electrical signal, optical signal, etc.).

Thus, in some examples, each of the one or more transceiver 120a-120n may comprise, respectively, a separate discrete transmitter 125 element and a separate discrete receiver 130 element, such as a speaker and a microphone. That is, each of the transmitter 125 and receiver 130 are two separate elements. Alternatively, the transmitter 125 and receiver 130 may be a single element. For example, in some embodiments, a single transducer element may be configured to be both a transmitter 125 and receiver 130. In other words, a single transducer element may both generate sound to be transmitted, and detect sound that has been received.

In various embodiments, each of the one or more array panels 110a-110n may include respectively the one or more driver circuits 115a-115n. The one or more driver circuit 115a-115n may be configured to drive a respective transceiver array 120. For example, in some embodiments, the one or more driver circuit 115a-115n may be configured to drive each respective transceiver 120a-120n. Each respective driver circuit 115a-115n may be configured to provide power to each respective transmitter 125a-125n and receiver 130a-130n of the transceiver array 120. In some examples, each of the one or more driver circuits 115a-115n may further comprise a respective power amplifier for driving transmitters 125 and line amplifiers to amplify a signal from each receiver 130. Thus, the first driver circuit 115a may comprise one or more power amplifiers for driving each of the one or more transmitters 125a-125n. The first driver circuit 115a may further comprise one or more line amplifiers for driving a respective signal from each of the receivers 130a-130n. In some embodiments, a single power amplifier may be configured to drive a single transmitter 125. Alternatively, in some examples, a single power amplifier may be configured to drive multiple transmitters 130. Similarly, in some embodiments, a single line amplifier may be configured to amplify a signal from a single receiver 130, while in other embodiments, a single line amplifier may be configured to amplify a signal from multiple receivers 130.

In various embodiments, each of the one more driver circuits 115a-115n may further respectively include one or more digital to analog converters (DACs) and one or more analog to digital converters (ADCs). In some embodiments, a single DAC may provide a signal to multiple transmitters 125 of the transceiver array 120, while in other embodiments, a single DAC may provide a signal to a single transmitter 125a-125n. Similarly, in some embodiments, a single ADC may be configured to convert a signal from multiple receivers 130 of the transceiver array 120, while in other embodiments, a single ADC may convert a signal from a single respective receiver 130a-130n.

In various embodiments, each array panel 110a-110n may include a back plate defining the back surface, and front plate defining the front surface. In some embodiments, the back plate may be configured to allow a printed circuit board (PCB) to be mounted. For example, in various embodiments, a PCB comprising the driver circuit 115a-115n and transceiver array may be mounted to the back plate. In some embodiments, the front plate may be protective screen, mesh, or cover to protect transmitter 125 elements and receiver 130 elements from physical contact and environmental damage (e.g., water, dust, etc.). In further embodiments, the front plate may be configured to be acoustically transparent, such that the front plate does not interfere with sound signals generated by the transmitters 125 or received by the receivers 130.

In some embodiments, the array panels 110 may be arranged such that each of the array panels 110a-110n faces inwards, with the front surfaces of each of the array panels may be positioned so as to face inwardly. For example, in a cube arrangement (e.g., six square-shaped array panels 110), each of the array panels 110a-110n may be positioned such that sound is transmitted into the volume defined by the six array panels 110 of the cube-shaped acoustic array 105. In other embodiments, depending on the application, the array panels 110 may be arranged to face outwards. Continuing with the cube-shaped example, each of the six array panels 110 may be positioned so as to transmit sound outwardly, away from the cube-shaped acoustic array 105. It is to be understood that inward and outward arrangements may be realized in differently shaped arrangements of the acoustic array 105 and utilizing differently shaped array panels 110.

Accordingly, in various embodiments, the one or more driver circuits 115a-115n may be configured to receive, from a controller 140, a probe signal to be generated by the transmitters 125a-125n of the transceiver array 120. As will be described in greater detail below with respect to FIG. 5, in some embodiments, the probe signal may be processed by the driver circuit 115a-115n such that a focused beam of sound is produced by the transceiver array. Similarly, the one or more driver circuits 115a-115n may be configured to process a received signal from the receivers 130 so as to receive sound from a focused area. In further embodiments, the controller 140 may generate an individual signal for each of the one or more transmitters 125a-125n, and further control each of the individual one or more receivers 130a-130n.

In various embodiments, the controller interface 135 may be configured to interface the controller 140 to the acoustic array 105. The controller interface 135 may include one or more interfaces for coupled to the controller 140 and one or more interfaces coupled to one or more array panels 110a-110n of the acoustic array 105. In some embodiments, for example, the controller interface 135 may include one or more universal serial bus (USB) interfaces coupled to a respective one or more USB physical layer (PHY) transceiver. In some embodiments, a first USB interface may be a dedicated input (from the controller 140), while a second USB interface may be a dedicated output (to the controller 140). The controller interface 135 may further include one or more optical interfaces coupled to one or more array panels 110a-110n. For example, the one or more optical interfaces may include a small form-factor pluggable (SFP) interface, including enhanced SFP (SFP+), and other suitable SFP interfaces. In some embodiments, a first SFP interface may be a dedicated input (from the acoustic array 105) and a second SFP interface may be a dedicate output (to the acoustic array). Thus, the controller interface 135 may include one or more optical PHY transceivers for driving the optical inputs/outputs. The controller interface 135 may, in various embodiments, include a processor, such as a signal processor (e.g., a digital signal processor (DSP), or other signal processor), field programmable gate array (FPGA), an application specific integrated circuit (IC), or other dedicated hardware configured to handle communications between the acoustic array 105 and the controller 105. For example, the processor may be configured to translate signal between the optical interface and the USB interface.

The controller interface 135 may further be configured to couple the power supply 145 to the acoustic array 105. For example, in some embodiments, the controller interface 135 may be configured to couple the power supply 145 to each of the driver circuits 115a-115n. In various embodiments, each of the driver circuits 115a-115n may include respective power management, such as a power management integrated circuit (PMIC) or other power controller as known to those skilled in the art. Therefore, the power supply 145 may be a power source configured to provide power to the acoustic array 105. The power supply 145 may include, for example, one or more batteries, wall power (e.g., mains power) from a utility grid, or other suitable power source. The power supply 145 may further include a power converter for converting between AC and/or DC power, voltage conversion, etc.

In various embodiments, the acoustic array 105 may be configured to accommodate various applications. For example, in various embodiments, suitable applications for acoustic array 105 may include, without limitation, high-speed train acoustic imaging, cancer cell acoustic monitoring research, remote heart monitoring, non-invasive high-speed 3D medical imaging, surface wave analysis for road and bridge defects, 3-D seismic imaging, shale and oil deposit identification fracking for oil/natural gas, ground imaging for tunnel boring machines, general purpose ground imaging from a moving vehicle, simultaneous monitoring of machinery equipment in factories, oil derricks, tunneling, vehicles, or other operations, monitoring/imaging of large structures, such as bridges, dams, tunnels, buildings, and foundations, sound reconstruction at long range or through walls, and imaging for security applications.

Figure 2:
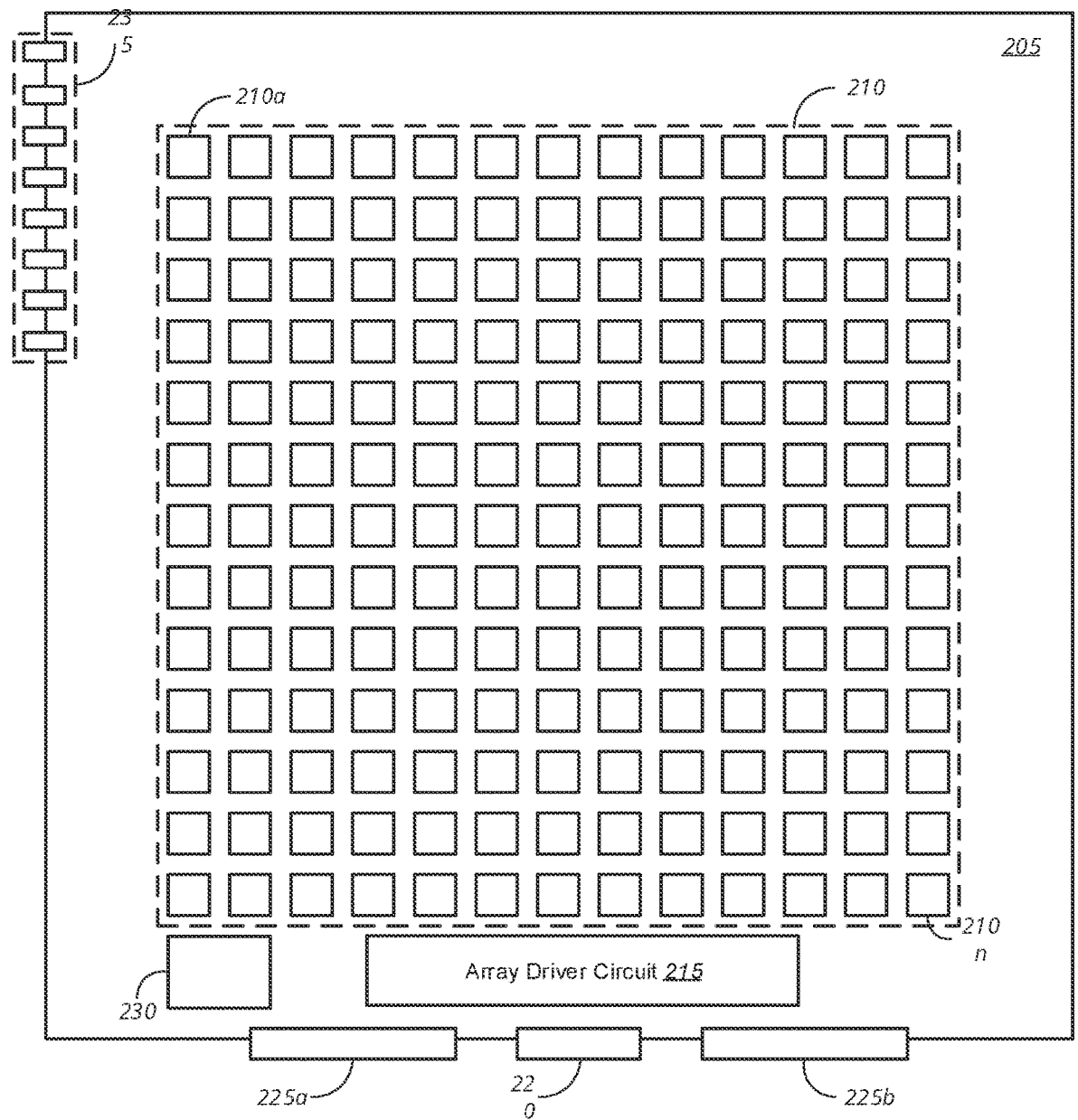
FIG. 2 is a schematic diagram of an array panel of the acoustic array, in accordance with various embodiments.

FIG. 2 is a schematic diagram of an array panel 200 of the acoustic array, in accordance with various embodiments. The array panel 200 includes housing 205, transceiver array 210, including one or more transceivers 210a-210n, array driver circuit 215, communication interface 220, input power interface 225a and output power interface 225b (collectively "power interfaces 225"), temperature sensor 230, and status LEDs 235. It should be noted that the various components of the array panel 200 are schematically illustrated in FIG. 2, and that modifications to the array panel 200 may be possible in accordance with various embodiments.

In various embodiments, the array driver circuit 215 may be coupled to each of the communication interface 220 and power interfaces 225. The driver circuit 215 may further be coupled to the temperature sensor 230, transceiver array 210, and status LEDs 235. In the depicted example, the transceiver array 210 may be a square-shaped array comprising 13 rows of 13 transceivers each, for a total of 169 transceivers 210a-210n.

In various embodiments, the array panel 200 includes communication interface 220 and power interfaces 225. In some embodiments, the communication interface 220 may be an optical interface, such as an SFP interface. The input power interface 225a may include one or more input interface via which power cables may be coupled. In some examples, the power interfaces 225 may be configured to provide 12V-24V DC power to the array panel 200. The output power interface 225*b* may include one or more output interfaces via which power cables may be coupled to provide power to a downstream array panel in the acoustic array.

In the illustrated embodiment, the array panel 200 includes eight status LEDs 235. The array panel 200 may, in some embodiments, further include a temperature sensor 230 configured to determine a temperature of one or more transceivers 210*a*-210*n*. For example, in some embodiments, the temperature sensor 230 may be configured to determine an average temperature for the array based on temperatures at the individual transceivers 210*a*-210*n*. The driver circuit 215 may, in some embodiments, may be configured to operate under a thermal protection mode in the event that the temperature reported by the temperature sensor 230 exceeds a threshold temperature. Accordingly, in various embodiments, the temperature sensor 230 may be configured to report measured temperatures to the array driver circuit 215.

In various embodiments, each of the one or more transceivers 210*a*-210*n* may be coupled to a PCB, which may in turn be coupled to the housing 205. The PCB may include respective connectors via which each individual transceiver 210*a*-210*n* may be coupled to the PCB. The array driver circuit 215 may, in turn, drive each individual transceiver 210*a*-210*n*.

Figure 3:
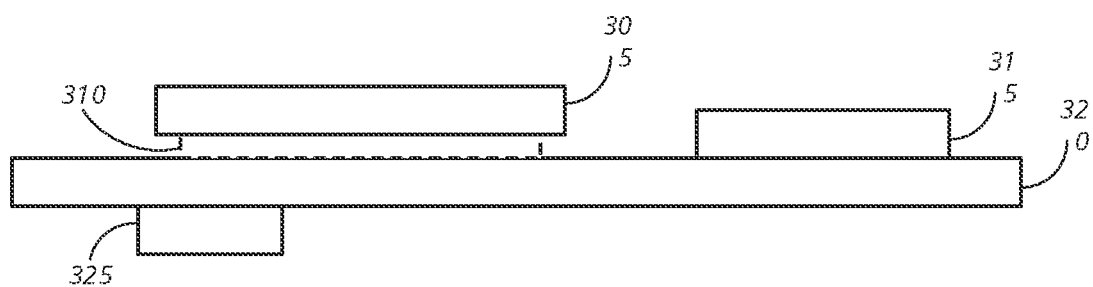
FIG. 3 is a cross-sectional schematic view of a transceiver, in accordance with various embodiments.

FIG. 3 is a cross-sectional schematic view of a transceiver 300, in accordance with various embodiments. The transceiver 300 includes speaker 305, dampener 310, microphone 315, sub-board 320, and connector 325. It should be noted that the various components of the transceiver 300 are schematically illustrated in FIG. 3, and that modifications to the transceiver 300 may be possible in accordance with various embodiments.

In various embodiments, the transmitter of the transceiver may be a separate element, in this case a speaker 305. The speaker 305 may be mounted directly to the sub-board 320. In some embodiments, a dampener 310 may be present between the speaker (e.g., the transducer) and the sub-board. For example, the dampener 310 may be configured to reduce vibration of the sub-board 230, and to mitigate unwanted aural effects, such as vibration/movement artifacts of the speaker 305. Similarly, the receiver of the transceiver may be a separate element, in this case microphone 315. The microphone 315 may similarly be mounted directly to the sub-board 320. The sub-board 320 may, in turn, further include a connector 325 configured to connect to a respective connector of the array panel.

Figure 4:
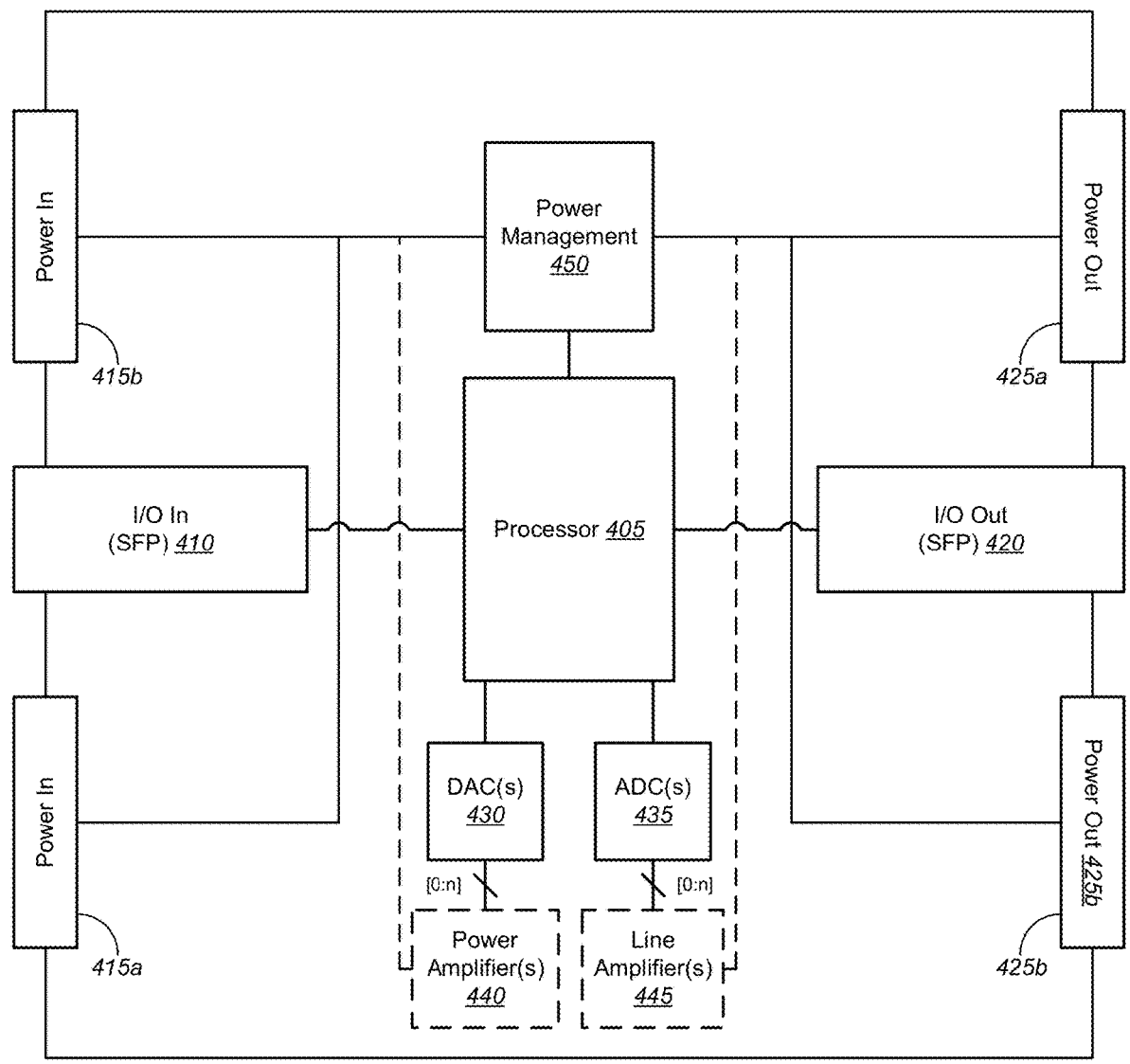
FIG. 4 is a schematic block diagram of an acoustic array driver circuit, in accordance with various embodiments.

FIG. 4 is a schematic block diagram of an acoustic array driver circuit 400, in accordance with various embodiments. The array driver circuit 400 includes a processor 405, input communication interface (I/O In) 410, first input power interface 415*a* and second input power interface 415*b* (collectively input power interfaces 415), output communication interface (I/O out) 420, first output power interface 425*a* and second output power interface 425*b* (collectively output power interfaces 425), one or more DACs 430, one or more ADCs 435, one or more power amplifiers 440, one or more line amplifiers 445, and power management section 450. It should be noted that the various components of the array driver circuit 400 are schematically illustrated in FIG. 4, and that modifications to the array driver circuit 400 may be possible in accordance with various embodiments.

In various embodiments, the processor 405 may be coupled to I/O in 410 and I/O out 420. The processor 405 may further be coupled to the one or more DACs 430 and one or more ADCs 435, and power management section 450. The one or more DACs 430 may be coupled to one or more power amplifiers 440, and the one or more ADCs 435 may be coupled to the one or more line amplifiers 445. The power management section 450 may be coupled to each of the input power interfaces 415 and output power interfaces 425. The power management section 450 may further be coupled to the one or more power amplifiers 440 and line amplifiers 445.

In various embodiments, the I/O In 410 includes both transmit (Tx) and receive (Rx) channels configured to communicate with a controller or alternatively an upstream array panel. I/O Out 420 includes both Tx and Rx channels configured to communication with a downstream array panel.

The processor 405 may include, without limitation, a suitable processor such as a microcontroller, FPGA, ASIC or other custom IC. Power management section 450 may include, without limitation, a PMIC, power converters, regulators, and the like. Each of the one or more power amplifiers 440 may be coupled to one or more respective transmitters of the one or more transceivers of the respective transceiver array. Similarly, the one or more line amplifiers 445 may be coupled to one or more respective receivers of the one or more transceivers of the respective transceiver array. The one or more power amplifiers 440 may be configured to amplify a probe signal from the controller, to be played by the one or more transmitters. Thus, in various embodiments, the one or more power amplifiers may drive (e.g., power) the one or more transmitters. The one or more line amplifiers 445 may be configured to amplify a captured signal received by the one or more receivers.

In an alternative arrangement, each of the one or more transceivers may comprise a respective power amplifier 440 and/or line amplifier 445, or both a power amplifier and line amplifier, coupled to a respective transmitter and/or receiver element. In various embodiments, the one or more power amplifiers 445 and/or the one or more line amplifiers 445 may be programmable gain amplifiers (PGAs). In some embodiments, each PGA may be configured to have multiple levels of gain control. For example, in some embodiments, the PGA may be configured to have 16 levels of gain control. In other embodiments, the PGA may be configured to have more or fewer gain control levels. In further embodiments, each subsequent gain level may double gain from a previous gain level.

In some embodiments gain can be set at the maximum signal level. In other embodiments, the gain may be set at a noise level if signal is below the noise level. Thus, a controller may be configured to cause the transmitter to generate a cancellation signal (e.g., transmitter signal) further configured to cancel incoming acoustic signals and correlated noise at each receiver element (e.g., microphone) to increase dynamic range. This may, in turn, lower both the noise and signal, allowing higher gain.

In some embodiments, a probe signal from the transmitter (e.g., speaker) may be combined with the cancellation signal, theoretically doubling the effective bits. For example, this technique can combine signals from the 24-bit DAC at the speaker and the 24-bit ADC at the microphone to obtain a 48-bit input signal. Signals from all microphones can be focused to increase the signal to noise ratio (SNR) by an additional 1014 times (~2^10), resulting in a dynamic range of 58 bits. In some imaging applications, probe signals from all speakers can also be focused, providing a total of 68-bits. Captured signals from each frequency can be combined.

Thus, 10,000 frequencies provide an additional 13-bits (81-bits). Captured signals over an 8 second range can provide an additional 3-bits (84-bits). Thus, results in signal amplification of 1.9E+25 (i.e., 19 trillion trillion) times, or by over 250 dB.

In various embodiments, the transceiver array may be configured to transmit a broadband signal. Thus, in some examples, a probe signal may be an acoustic signal with one or more frequency elements, or a range of frequency elements. Accordingly, transmission of a broadband signals may increase resolution proportional to the frequency bandwidth, the scatter level, and the transceiver spacing. Moreover, a broadband probe signal may overcome resolution limitations of using lower frequencies, while lower frequency elements have a lower attenuation rate/high penetration than ultrasound and other high frequency elements. Moreover, lower frequency acoustic signals have increased range, and do not require an acoustic couplant, such as ultrasound gel.

Thus, by utilizing a broadband signal, higher resolution may be obtained in various mediums with sufficient scatter and reflectors, such as biological tissue or geologic lithology. Higher frequencies attenuate faster than lower frequencies, resulting in a lower scatter rate and narrower Fresnel zone. The Fresnel zone is a region in the medium that influences the signal between a source/reflector and a receiver. The Fresnel zone is elliptical in a homogenous medium, but may curve and split into multiple regions in a medium with variable acoustic refractive characteristics (e.g., velocity of sound propagation). In such environments, the resolution may be proportional to the difference between Fresnel zone regions.

For example, a first Fresnel zone may be a Fresnel zone at a first frequency, and a second Fresnel zone may be a Fresnel zone at a second frequency. In one example, the first Fresnel zone may be associated with a signal at 10,001 Hz, and the second Fresnel zone may be associated with a signal at 10,000 Hz. In a homogenous medium, such as air between a speaker on the top panel and a microphone on the bottom panel, the Fresnel zone may be elliptical as described above. At the example frequencies, the second Fresnel zone may be slightly larger than the first Fresnel zone.

If both of these frequencies are sent simultaneously from the same speaker and received by the same microphone, the difference in the Fresnel regions can be obtained in the captured signal. Thus, extremely high three-dimensional (3-D) resolutions can be obtained by using thousands of different frequencies and millions of different source/reflector-receiver pairs, in a fraction of a second. This technique significantly increases 3-D resolution both inside and outside the cube by using the full range of available frequencies (10 Hz-10 kHz), active sources from the speakers, passive sources/noise within range, and any detected reflectors.

Figure 5:
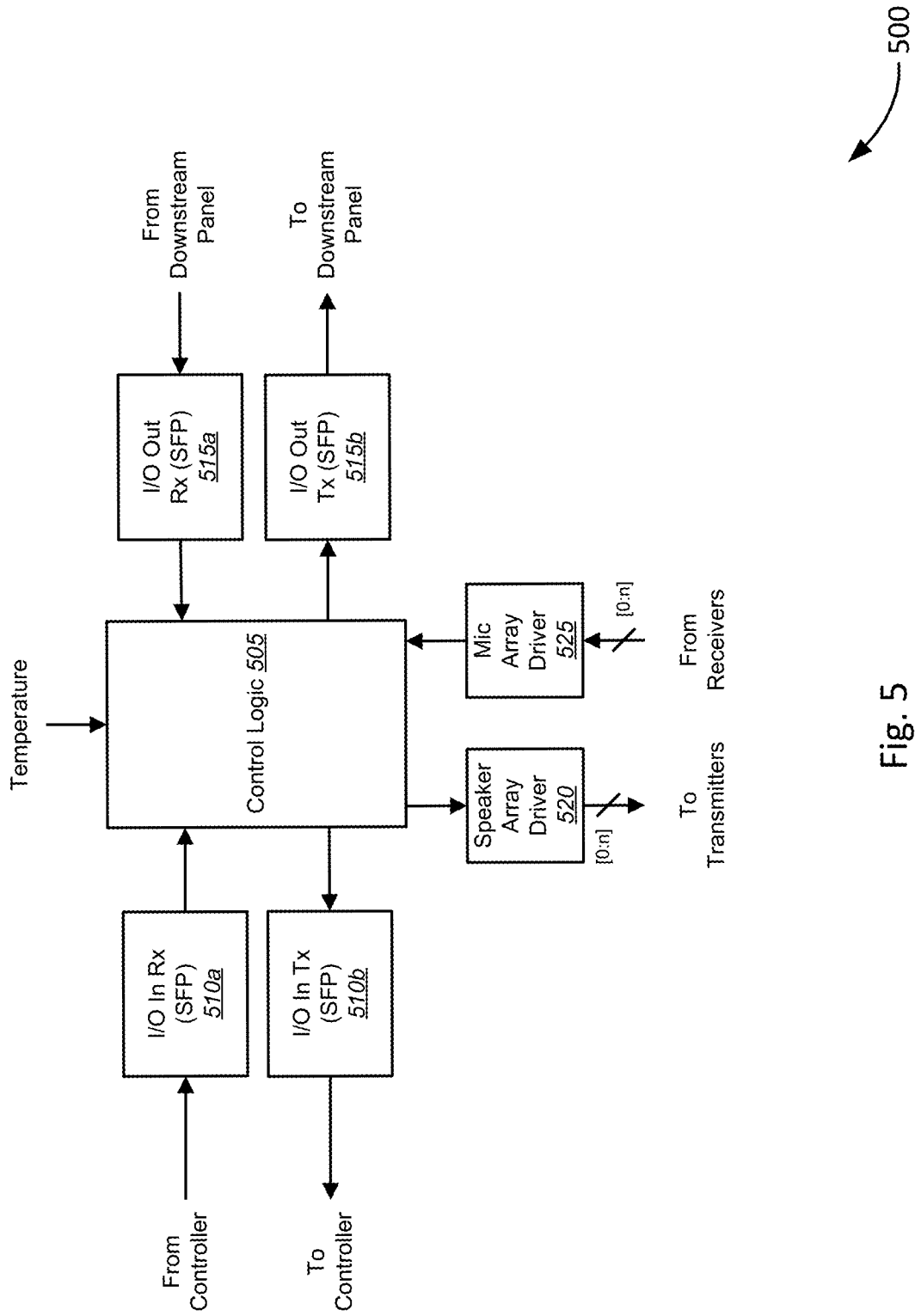
FIG. 5 is a functional block diagram of the acoustic array driver circuit, in accordance with various embodiments.

FIG. 5 is a functional block diagram of the acoustic array driver circuit 500, in accordance with various embodiments. Specifically, the acoustic array driver circuit 500 includes control logic 505, I/O In Rx channel 510a, I/O In Tx channel 510b, I/O Out Rx channel 515a, I/O out Tx channel 515b, speaker array driver section 520, and mic array driver section 525.

With reference to FIGS. 4 & 5, in various embodiments, control logic 505 may be executed on processor 405 of the array driver circuit 400, 500. The control logic 505 may receive, as input, from the controller or an upstream array panel, a probe signal to be played by the transmitters of the transceiver array. In some embodiments, the control logic 505 may further receive instructions for beam focusing a signal to be generated by the transmitters of the transceiver array (also referred to as a speaker array in FIG. 5). Similarly, control logic 505 may further receive instructions for focusing a received signal from the receivers of the transceiver array (also referred to as a mic array). Control logic 505 may further receive, as inputs, a temperature from a temperature sensor of the array panel. Control logic 505 may receive, from a downstream panel, a captured signal from the receivers of the transceiver array of the downstream panel. The control logic 505 may, therefore, be configured to transmit the captured signal upstream to the controller and/or an upstream array panel. Control logic 505 may similarly be configured to transmit the probe signal further downstream to a subsequent downstream panel via the I/O Out Tx channel 515b.

In various embodiments, the control logic 505 may further be configured to transmit the probe signal to the speaker array driver section 520. The speaker array driver section 520 may be configured convert the probe signal into an analog signal to be played by the one or more transmitters of the transceiver array. In some embodiments, the control logic 505 may be configured to beam-focus the probe signal. For example, in some embodiments, the control logic 505 may output a respective probe signal individually to each transmitter of the transceiver array, each respective probe signal having a respective delay configured to create a focused beam. Similarly, the mic array driver section 525 may be controlled, via the control logic 505, to capture sound from a desired area.

Figure 6:
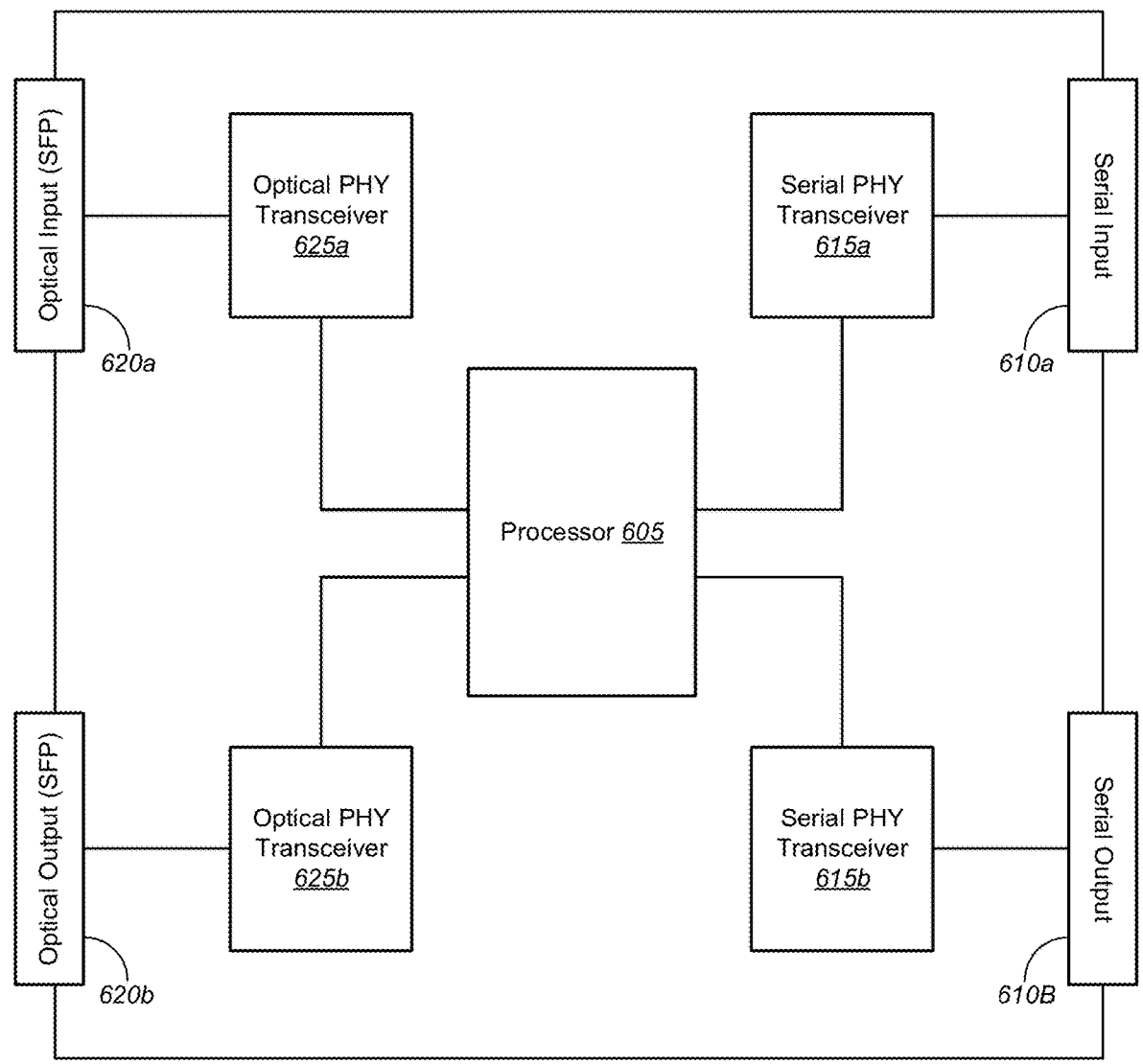
FIG. 6 is a schematic block diagram of an acoustic array controller interface, in accordance with various embodiments.

FIG. 6 is a schematic block diagram of an acoustic array controller interface 600, in accordance with various embodiments. The controller interface 600 includes processor 605, input serial interface 610a and output serial interface 610b (collectively "serial interfaces 610"), input serial PHY transceiver 615a and output serial PHY transceiver 615b, input optical interface 620a and output optical interface 620b (collectively "optical interfaces 620"), input optical PHY transceiver 625a and output optical PHY transceiver 625b. It should be noted that the various components of the controller interface 600 are schematically illustrated in FIG. 6, and that modifications to the controller interface 600 may be possible in accordance with various embodiments.

In various embodiments, the processor 605 may be coupled to the input serial interface 610a via the input serial PHY transceiver 615a, the output serial interface 610b via the output serial PHY transceiver 615b, the input optical interface 620a via the input optical PHY transceiver 625a, and the output optical interface 620b via the output optical PHY transceiver 625b.

The controller interface 600 may be configured to interface a controller to the acoustic array. Accordingly, the processor 605 may be configured to handle communications to and from the controller via the serial interfaces 610, and to and from the acoustic array via the optical interfaces 620. The processor 605 may further be configured to allow communications between the controller and the acoustic array. Specifically, data received from the input serial interface 610a, such as a probe signal, may be transmitted to a first array panel via the output optical interface 620b. Similarly, data received from the acoustic array, via the input optical interface 620a, may be transmitted to the controller via the output serial interface 610b. Thus, optical signals may be transmitted via a serial interface, and serial signals may be transmitted via the optical interface by the processor 605.

In some embodiments, the serial interfaces 610 may be two respective USB interfaces, each USB interface exclusively comprising an input channel and output channel respectively. Alternatively, each USB interface may be configured to carry both input and output communication. Similarly the optical interfaces 620 may be two respective SFP interfaces, each SFP comprising, respectively, an input and output channel. Alternatively, each SFP may exclusively handle one of input communications or output communications.

Figure 7:
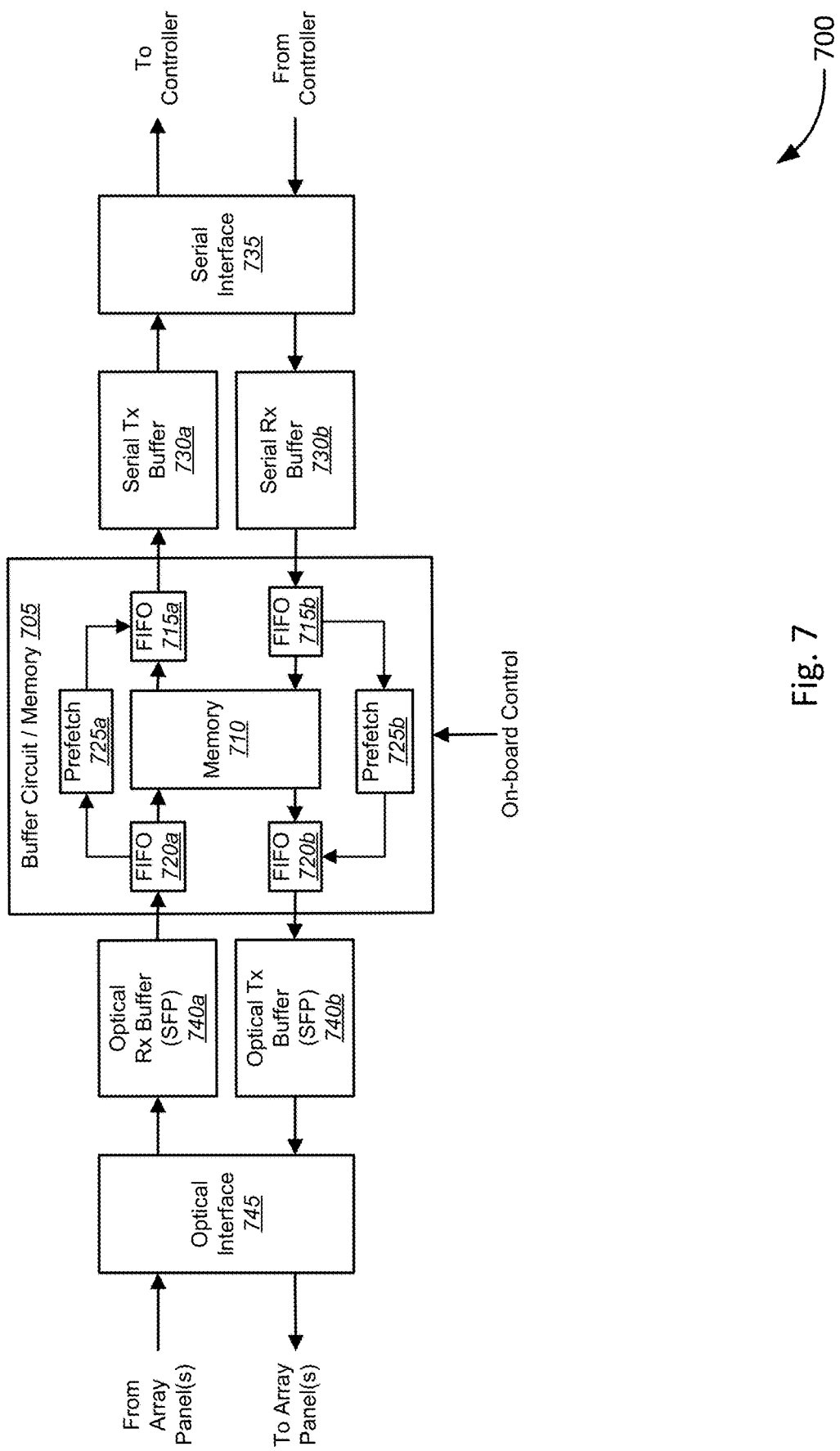
FIG. 7 is a functional block diagram of the acoustic array controller interface, in accordance with various embodiments.

FIG. 7 is a functional block diagram of the acoustic array controller interface 700, in accordance with various embodiments. The controller interface 700 may include a buffer circuit/memory 705, memory IC 710, FIFO buffers 715*a*, 715*b*, 720*a*, 720*b*, prefetch buffers 725*a*, 725*b*, serial Tx buffer 730*a*, serial Rx buffer 730*b*, serial interface 735, optical RX buffer 740*a*, optical Tx buffer 740*b*, and optical interface 745.

According to various embodiments, for communication from the controller, data from the serial interface 735 is received at the serial Rx buffer 730*b*. Data from the serial Rx buffer 730*b* may be read into the buffer circuit 705. For example, data from the serial Rx buffer 730*b* may be read into FIFO 715*b* of a memory module 705. Data from the FIFO 715*b* is, in turn, read into memory IC 710. In some examples, data from the FIFO 715*b* may further be pre-fetched and stored in the pre-fetch buffer 725*b*. Data from the pre-fetch buffer 725*b* may be read into the FIFO 720*b*, and if all data from the pre-fetch buffer 725*b* has been read in, data from memory IC 710 may be read into the FIFO 720*b*. Data from FIFO 720B may then be read into the optical Tx buffer 740*b*, for transmission via the optical interface 745 to the first array panel.

In various embodiments, for communication from the array panel, data may be received from the optical interface 745 and stored in the optical Rx buffer 740*a*. Data from the optical Rx buffer 740*a* may be read into the buffer circuit/ memory 705. Specifically, data from the optical Rx buffer 740*a* is read into the FIFO 720*a*. Data from FIFO 720*a* may be pre-fetched and stored in pre-fetch buffer 725*a*. Remaining data from the FIFO 720*a* may then be written to the memory IC 710. FIFO 715*a* then receives data from the pre-fetch buffer 725*a* to be read out to the serial Tx buffer 730*a*. Once pre-fetch data has been transmitted, data may be read out from memory IC 710 into the FIFO 715*a*, and to the serial Tx buffer 730*a* for transmission over the serial interface 735.

Figure 8:
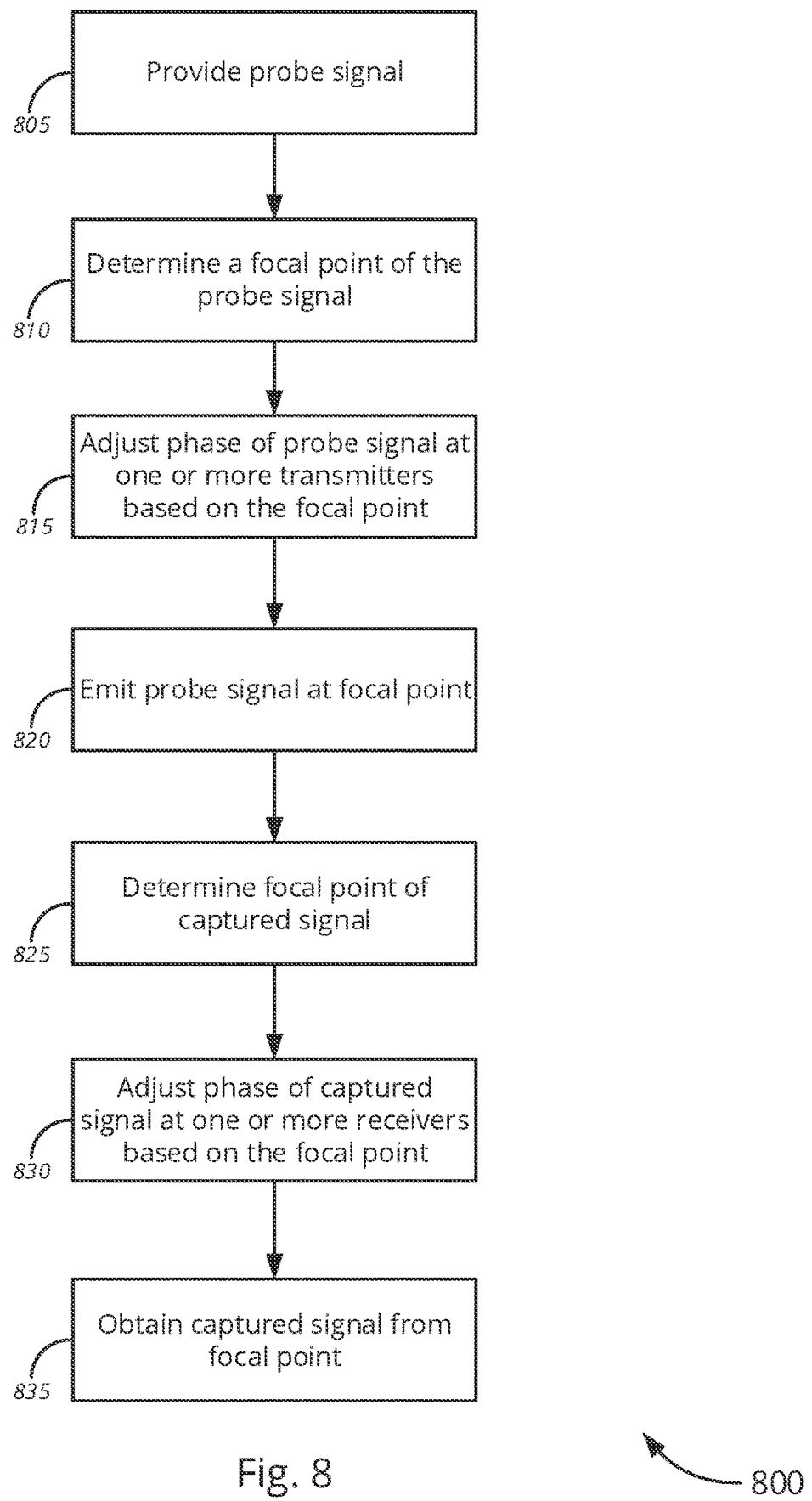
FIG. 8 is a flow diagram of a method for acoustic array detection and imaging, in accordance with various embodiments.

FIG. 8 is a flow diagram of a method 800 for acoustic array detection and imaging, in accordance with various embodiments. The method 800 may begin, at block 805, by receiving, from a controller, a probe signal to be transmitted by the transceiver array. In various embodiments, each of the one or more driver circuits of the one or more array panels may be configured to receive the probe signal from the controller or from an upstream array panel.

The method 800 continues, at block 810, by determining a focal point of the probe signal. In some embodiments, the probe signal may further indicate a focal point for the probe signal. For example, a user may control a focal point of the probe signal via the controller. Accordingly, in some embodiments, instructions for controlling the focal point may be included with the probe signal and/or separately transmitted to each of the one or more driver circuits.

The method 800 continues, at block 815, by adjusting a phase of the probe signal at one or more transmitters based, at least in part, on the focal point. For example, in some embodiments, the one or more driver circuits may be configured to determine a phase delay for each probe signal of each individual transmitter of the transceiver array. As previously described, in other embodiments, the driver circuit may receive a respective probe signal for each individual transmitter of the transceiver array directly from the controller. Thus, the focal point may be controlled at either the driver circuit or the controller by adjustment of the phase of the probe signal (e.g., time delay) at each of the transmitter elements of the transceiver array.

The method 800, at block 820, continues by emitting the probe signal at the focal point. As will be appreciated by those skilled in the art, by adjusting the phase of the probe signal at different transmitter elements of the transceiver array, the beam of sound (e.g., the probe signal) projected by the transceiver array may be steered in three-dimensional space.

The method 800 continues by determining, at block 825, a focal point from which to obtain a captured signal via the receiver elements of the transceiver array. In various embodiments, each of the one or more driver circuits of the one or more array panels may be configured to receive instructions for obtaining a captured signal from a focal point from the control or from an upstream array panel. In some embodiments, the focal point may be the same focal point as the focal point of the probe signal. Thus, the captured signal may be obtained from the same focal point as where the probe signal is emitted.

The method 800 continues, at block 830, by adjusting a phase of the captured signal at one or more of the receivers based, at least in part, on the focal point. For example, in some embodiments, the one or more driver circuits may be configured to determine a phase delay for each captured signal from each individual receiver of the transceiver array. As previously described, in other embodiments, the driver circuit may receive phase adjustment instructions for each captured signal from each individual receiver of the transceiver array directly from the controller. Thus, the focal point may be controlled at either the driver circuit or by the controller via adjustment of the phase of the captured signal (e.g., time delay) at each receiver element of the transceiver array.

The method 800, at block 830, continues by obtaining the captured signal at the focal point. As will be appreciated by those skilled in the art, by adjusting the phase of the probe signal at different receiver elements of the transceiver array, the focal point from which sound is captured (e.g., captured signal) may be steered in three-dimensional space.

Figure 9:
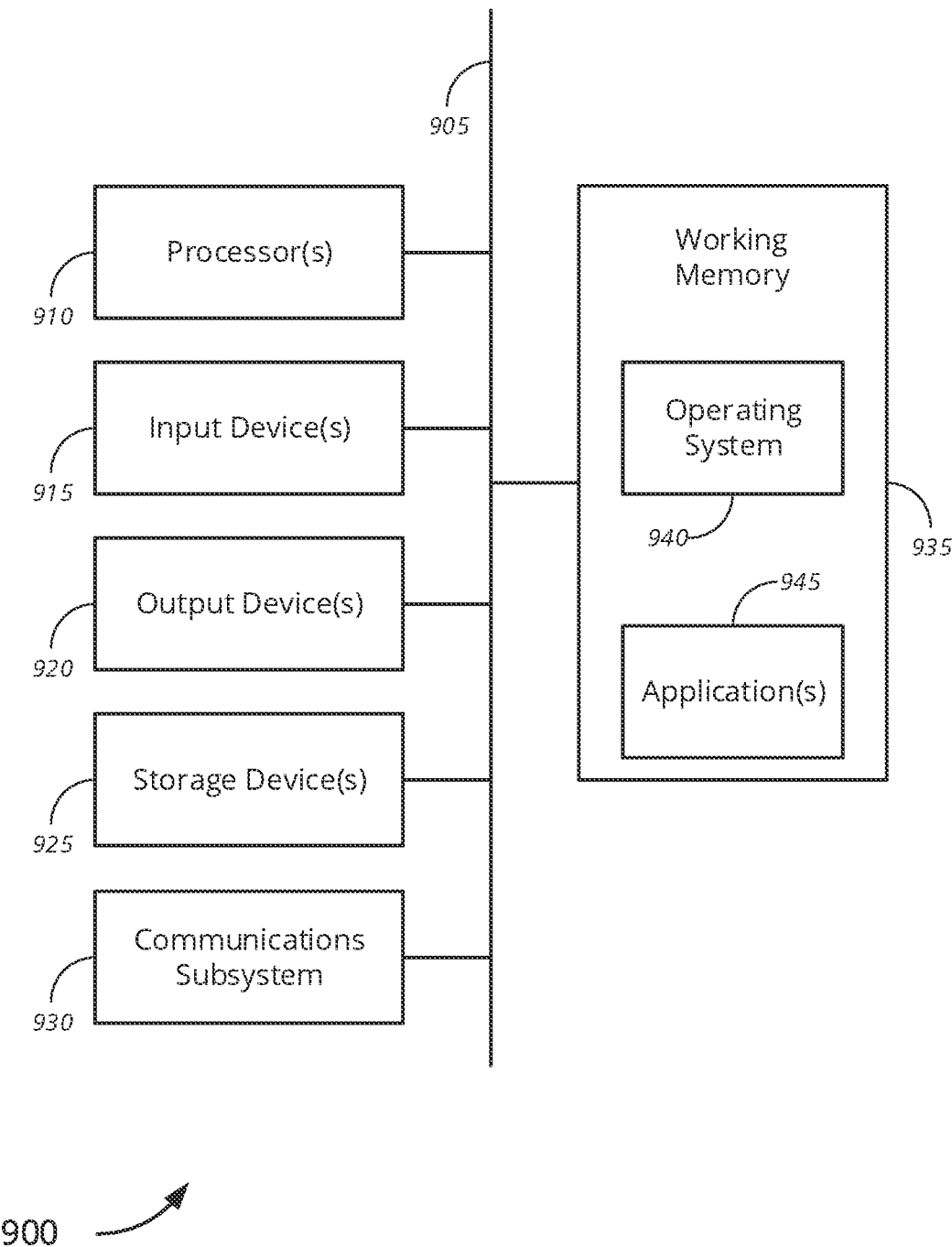
FIG. 9 is a schematic block diagram of a computer system for acoustic array detection and imaging, in accordance with various embodiments.

FIG. 9 is a schematic block diagram of a computer system 900 for acoustic array detection and imaging, in accordance with various embodiments. FIG. 9 provides a schematic illustration of one embodiment of a computer system 900, such as the controller, control interface, one or more array panels, and/or driver circuits of the one or more array panels, which may perform the methods provided by various other embodiments, as described herein. It should be noted that FIG. 9 only provides a generalized illustration of various components, of which one or more of each may be utilized as appropriate. FIG. 9, therefore, broadly illustrates how individual system elements may be implemented in a relatively separated or relatively more integrated manner.

The computer system 900 includes multiple hardware elements that may be electrically coupled via a bus 905 (or may otherwise be in communication, as appropriate). The hardware elements may include one or more processors 910, including, without limitation, one or more general-purpose processors and/or one or more special-purpose processors (such as microprocessors, digital signal processing chips, graphics acceleration processors, and microcontrollers); one or more input devices 915, which include, without limitation, a mouse, a keyboard, one or more sensors, and/or the like; and one or more output devices 920, which can include, without limitation, a display device, and/or the like.

The computer system 900 may further include (and/or be in communication with) one or more storage devices 925, which can comprise, without limitation, local and/or network accessible storage, and/or can include, without limitation, a disk drive, a drive array, an optical storage device, solid-state storage device such as a random-access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer system 900 might also include a communications subsystem 930, which may include, without limitation, a modem, a network card (wireless or wired), an IR communication device, a wireless communication device and/or chip set (such as a Bluetooth™ device, an 802.11 device, a WiFi device, a WiMax device, a WWAN device, a Z-Wave device, a ZigBee device, cellular communication facilities, etc.), and/or a LP wireless device as previously described. The communications subsystem 930 may permit data to be exchanged with a network (such as the network described below, to name one example), with other computer or hardware systems, between data centers or different cloud platforms, and/or with any other devices described herein. In many embodiments, the computer system 900 further comprises a working memory 935, which can include a RAM or ROM device, as described above.

The computer system 900 also may comprise software elements, shown as being currently located within the working memory 935, including an operating system 940, device drivers, executable libraries, and/or other code, such as one or more application programs 945, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 925 described above. In some cases, the storage medium might be incorporated within a computer system, such as the system 900. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer system 900 and/or might take the form of source and/or installable code, which, upon compilation and/or installation on the computer system 900 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, single board computers, FPGAs, ASICs, and SoCs) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer system 900) to perform methods in accordance with various embodiments of the invention. According to a set of embodiments, some or all of the procedures of such methods are performed by the computer system 900 in response to processor 910 executing one or more sequences of one or more instructions (which might be incorporated into the operating system 940 and/or other code, such as an application program 945) contained in the working memory 935. Such instructions may be read into the working memory 935 from another computer readable medium, such as one or more of the storage device(s) 925. Merely by way of example, execution of the sequences of instructions contained in the working memory 935 might cause the processor(s) 910 to perform one or more procedures of the methods described herein.

The terms "machine readable medium" and "computer readable medium," as used herein, refer to any medium that participates in providing data that causes a machine to operate in a specific fashion. In an embodiment implemented using the computer system 900, various computer readable media might be involved in providing instructions/code to processor(s) 910 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 925. Volatile media includes, without limitation, dynamic memory, such as the working memory 935. In some alternative embodiments, a computer readable medium may take the form of transmission media, which includes, without limitation, coaxial cables, copper wire and fiber optics, including the wires that comprise the bus 905, as well as the various components of the communication subsystem 930 (and/or the media by which the communications subsystem 930 provides communication with other devices). In an alternative set of embodiments, transmission media can also take the form of waves (including, without limitation, radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 910 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 900. These signals, which might be in the form of electromagnetic signals, acoustic signals, optical signals, and/or the like, are all examples of carrier waves on which instructions can be encoded, in accordance with various embodiments of the invention.

The communications subsystem 930 (and/or components thereof) generally receives the signals, and the bus 905 then might carry the signals (and/or the data, instructions, etc. carried by the signals) to the working memory 935, from which the processor(s) 910 retrieves and executes the instructions. The instructions received by the working memory 935 may optionally be stored on a storage device 925 either before or after execution by the processor(s) 910.

Figure 10:
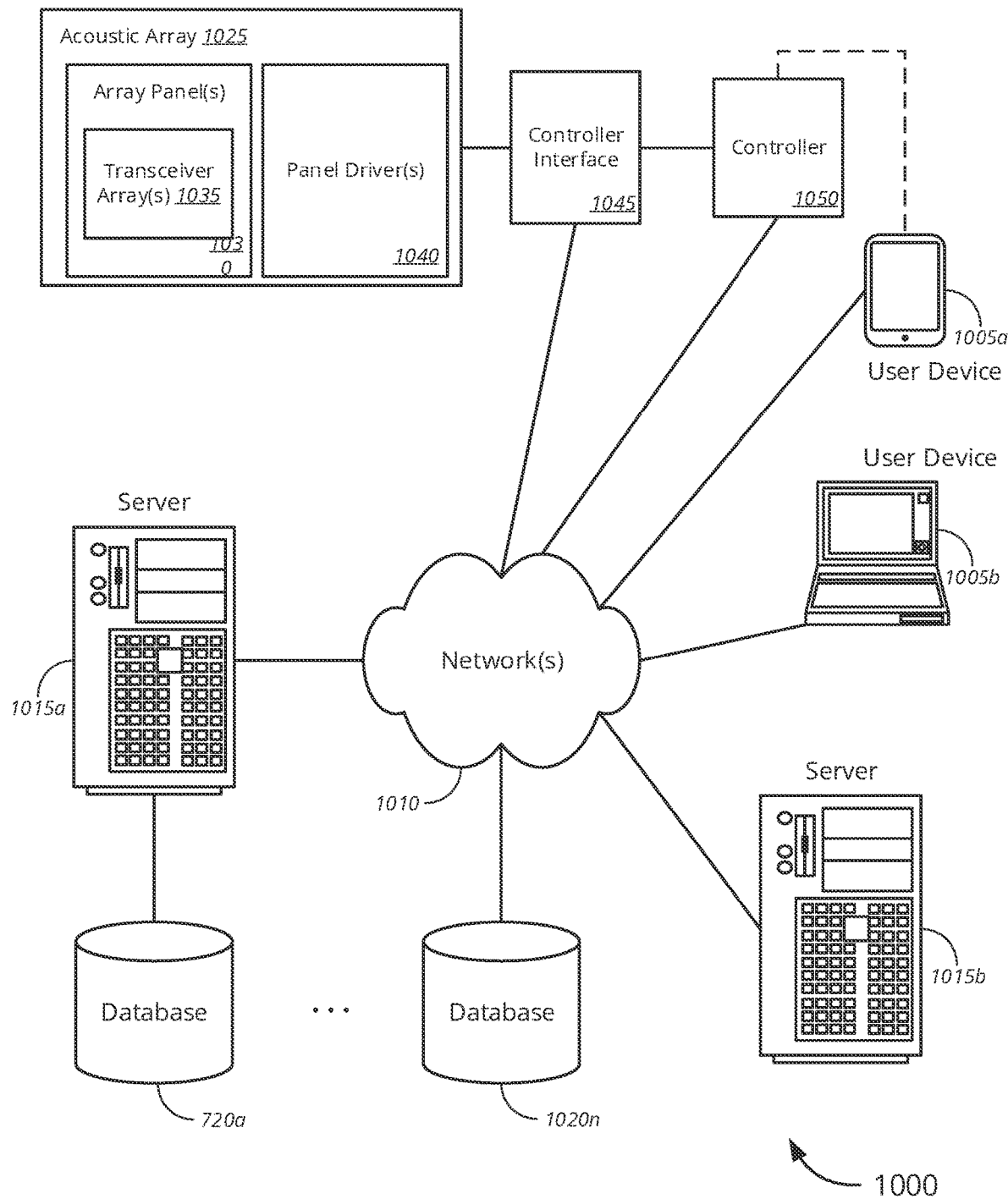
FIG. 10 is a block diagram illustrating a networked system of computing systems, which may be used in accordance with various embodiments.

FIG. 10 is a block diagram illustrating a networked system of computing systems, which may be used in accordance with various embodiments. The system 1000 may include one or more user devices 1005. A user device 1005 may include, merely by way of example, desktop computers, single-board computers, tablet computers, laptop computers, handheld computers, and the like, running an appropriate operating system. User devices 1005 may further include external devices, remote devices, servers, and/or workstation computers running any of a variety of operating systems. In some embodiments, the operating systems may include commercially-available UNIX™ or UNIX-like operating systems. A user device 1005 may also have any of a variety of applications, including one or more applications configured to perform methods provided by various embodiments, as well as one or more office applications, database client and/or server applications, and/or web browser applications. Alternatively, a user device 1005 may include any other electronic device, such as a thin-client computer, Internet-enabled mobile telephone, and/or personal digital assistant, capable of communicating via a network (e.g., the network(s) 1010 described below) and/or of displaying and navigating web pages or other types of electronic documents. Although the exemplary system 1000 is shown with two user devices 1005, any number of user devices 1005 may be supported.

Certain embodiments operate in a networked environment, which can include a network(s) 1010. The network(s) 1010 can be any type of network familiar to those skilled in the art that can support data communications using any of a variety of commercially-available (and/or free or proprietary) protocols, including, without limitation, MQTT, CoAP, AMQP, STOMP, DDS, SCADA, XMPP, custom middleware agents, Modbus, BACnet, NCTIP 1213, Bluetooth, Zigbee/Z-wave, TCP/IP, SNA™ IPX™, AppleTalk™, and the like. Merely by way of example, the network(s) 1010 can each include a local area network ("LAN"), including, without limitation, a fiber network, an Ethernet network, a Token-Ring™ network and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, management network, and/or the Internet.

Embodiments can also include one or more server computers 1015. Each of the server computers 1015 may be configured with an operating system, including, without limitation, any of those discussed above, as well as any commercially (or freely) available server operating systems. Each of the servers 1015 may also be running one or more applications, which can be configured to provide services to one or more clients 1005 and/or other servers 1015.

Merely by way of example, one of the servers 1015 might be a data server, a web server, a cloud computing device(s), or the like, as described above. The data server might include (or be in communication with) a web server, which can be used, merely by way of example, to process requests for web pages or other electronic documents from user computers 1005. The web server can also run a variety of server applications, including HTTP servers, FTP servers, CGI servers, database servers, Java servers, and the like. In some embodiments of the invention, the web server may be configured to serve web pages that can be operated within a web browser on one or more of the user computers 1005 to perform methods of the invention.

The server computers 1015, in some embodiments, might include one or more application servers, which can be configured with one or more applications, programs, webbased services, or other network resources accessible by a client. Merely by way of example, the server(s) 1015 can be one or more general purpose computers capable of executing programs or scripts in response to the user computers 1005 and/or other servers 1015, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 1005 and/or another server 1015. In some embodiments, an application server can perform one or more of the processes for implementing media content streaming or playback, and, more particularly, to methods, systems, and apparatuses for implementing video tuning and wireless video communication using a single device in which these functionalities are integrated, as described in detail above. Data provided by an application server may be formatted as one or more web pages (comprising HTML, JavaScript, etc., for example) and/or may be forwarded to a user computer 1005 via a web server (as described above, for example). Similarly, a web server might receive web page requests and/or input data from a user computer 1005 and/or forward the web page requests and/or input data to an application server. In some cases, a web server may be integrated with an application server.

In accordance with further embodiments, one or more servers 1015 can function as a file server and/or can include one or more of the files (e.g., application code, data files, etc.) necessary to implement various disclosed methods, incorporated by an application running on a user computer 1005 and/or another server 1015. Alternatively, as those skilled in the art will appreciate, a file server can include all necessary files, allowing such an application to be invoked remotely by a user computer, user device, or customer device 1005 and/or server 1015.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 1020a-1020n (collectively, "databases 1020"). The location of each of the databases 1020 is discretionary: merely by way of example, a database 1020a might reside on a storage medium local to (and/or resident in) a server 1015a (or alternatively, user device 1005). Alternatively, a database 1020n can be remote from any or all of the computers so long as it can be in communication (e.g., via the network 1010) with one or more of these. In a particular set of embodiments, a database 1020 can reside in a storage-area network ("SAN") familiar to those skilled in the art. (Likewise, any necessary files for performing the functions attributed to the computers can be stored locally on the respective computer and/or remotely, as appropriate.) In one set of embodiments, the database 1020 may be a relational database configured to host one or more data lakes collected from various data sources, user devices 1005, or other sources. Relational databases may include, for example, an Oracle database, that is adapted to store, update, and retrieve data in response to SQL-formatted commands. The database might be controlled and/or maintained by a database server.

The system 1000 may further include an acoustic array 1025, further including the one or more array panels 1030 and a panel driver circuit 1040, each of the one or more array panels comprising a respective transceiver array 1035, a controller interface 1045, and controller 1050. In various embodiments, the acoustic array 1025 may be coupled, via the controller interface 1045, to the controller 1050.

In some embodiments, as previously describer, the controller 1050 may be coupled to the controller interface via a serial interface, such as a USB interface. The acoustic array 1025 may be coupled to the controller interface via an optical interface, such as an SFP interface, as previously described. In other embodiments, the controller 1050 may eb coupled to the controller interface 1045 via the network 1010. Similarly, the controller interface 1045 may include a network interface via which the controller interface 1045 is coupled to the network 1010. In some embodiments, one or more user devices may be coupled to the controller 1050 and/or network 1010. Thus, a user may be able to see results from the controller 1050 and/or control the acoustic array 1025 via the controller 1050 from a user device 1005a.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to certain structural and/or functional components for ease of description, methods provided by various embodiments are not limited to any single structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in sequentially for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a specific structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to one embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system comprising:
    an acoustic array of 1014 acoustic transceivers, comprising six array panels, each of the array panels comprising a transceiver array of 169 acoustic transceivers, each acoustic transceiver further comprising:
        a transmitter element configured to generate sound;
        a receiver element to capture sound;
        a 24-bit digital to analog converter (DAC) to convert a digital signal to an analog signal for transmission by the transmitter element; and
        a 24-bit analog to digital converter to convert an analog signal from the receiver element to a digital signal;
    a driver circuit coupled with the plurality of acoustic array, the driver circuit configured to drive individually each transmitter element and each receiver element of each transceiver array;
    a controller interface coupled to the driver circuit;
    a controller coupled to the controller interface, the controller comprising:
        a processor; and
        non-transitory computer readable media comprising instructions executable by the processor to:
            provide, via the controller interface, a probe signal to the driver circuit;
            provide, via the controller interface, a cancellation signal to the driver input, to cancel incoming acoustic signals and correlated noise at each receiver element of the acoustic array;
            provide, via the controller interface, a transmit focal point for the probe signal to be transmitted by the acoustic array;
            adjust, via the driver circuit, a first phase of the probe signal at one or more transmitter elements of the acoustic array based on the focal point; and
            emit, via the acoustic array, the probe signal at the focal point, wherein the probe signal is a broadband signal comprising a plurality of frequencies within a frequency band ranging from 10 Hz to 10 kHz, each of the acoustic transceivers transmitting 10,000 frequencies within the plurality of frequencies;

emit, via the acoustic array, the cancellation signal;
receive, via the controller interface, a plurality of digital signals, the plurality of signals comprising:
a first 24-bit digital signal for each of the 10,000 frequencies from the DAC of each transceiver;
a second 24-bit signal for each of the 10,000 frequencies from the ADC of each transceiver; and produce a high-resolution, three-dimensional signal with 84 bits of dynamic resolution from the plurality of digital signals by performing the following operations:
for each transceiver, combine the first 24-bit digital signal with the second 24-bit digital signal to produce a single-frequency transceiver signal having 48 bits of dynamic range per frequency per transceiver;
for each of the 10,000 frequencies, combine the single-frequency transceiver signal of each transceiver to produce a combined single-frequency signal having 68 bits of dynamic range per frequency;
combine each of the 10,000 single frequency signals to produce a multi-frequency signal having 81 bits of dynamic range; and
combine a plurality of multi-frequency signals received over a duration of eight seconds to produce the high-resolution, three-dimensional signal.

2. The system of claim 1, wherein the instructions are further executable by the processor to:
determine the transmit focal point for the probe signal based on user input.

3. The system of claim 1, wherein the instructions are further executable by the processor to:
provide, via the controller interface, a respective probe signal for each individual transmitter element of the first transceiver array, each probe signal having a respective phase delay based, at least in part, on the transmit focal point.

4. The system of claim 1, wherein the driver circuit is further configured to determine, based on the transmit focal point, a respective adjustment of the phase of the probe signal for each of the one or more transmitter elements of the first transceiver array.

5. The system of claim 1, wherein the instructions are further executable by the processor to:
determine a receive focal point of a captured signal;
provide, via the controller interface, the receive focal point for the captured signal to be obtained by the first transceiver array;
adjust, via the driver circuit, a second phase of the captured signal at one or more receiver elements of the first transceiver array based on the receive focal point; and
obtain, via the first transceiver array, the captured signal from the receive focal point.

6. The system of claim 5, wherein the receive focal point and transmit focal point are the same point in three-dimensional space.

7. The system of claim 5, wherein the instructions are further executable by the processor to:
determine the receive focal point for the probe signal based on user input.

8. The system of claim 5, wherein the instructions are further executable by the processor to:

provide, via the controller interface, a respective phase delay for each respective captured signal from each individual receiver element of the first transceiver array, each captured signal having a respective phase delay based, at least in part, on the receive focal point.

9. The system of claim 1, wherein acoustic array comprises six square shaped array panels arranged in a cube-shaped structure, each of the six square-shaped array panels defining a surface of the cube-shaped structure; wherein each array panel comprises a respective square-shaped transceiver array.

10. The system of claim 1, wherein the controller interface is coupled to the controller via a serial interface, wherein the controller interface is coupled to the driver circuit via an optical interface.

11. The system of claim 1, wherein the transmitter element and the receiver element of each transceiver is a single transducer element.

12. An apparatus comprising:
a processor;
non-transitory computer readable media comprising instructions executable by the processor to:
provide a probe signal to a driver circuit of an acoustic array of 1014 acoustic transceivers, the acoustic array comprising six array panels, each of the array panels including a respective transceiver array, each transceiver array comprising 169 transceivers, each transceiver comprising:
a transmitter element;
a receiver element;
a 24-bit digital to analog converter (DAC) to convert a digital signal to an analog signal for transmission by the transmitter element; and
a 24-bit analog to digital converter to convert an analog signal from the receiver element to a digital signal;
provide a cancellation signal to the driver input, to cancel incoming acoustic signals and correlated noise at each receiver element of the acoustic array;
provide a transmit focal point for the probe signal to be transmitted by the acoustic array;
adjust, via the driver circuit of the acoustic array, a first phase of the probe signal at one or more transmitter elements of the acoustic array based on the focal point;
emit, via the acoustic array, the probe signal at the focal point, wherein the probe signal is a broadband signal comprising a plurality of frequencies within a frequency band ranging from 10 Hz to 10 kHz, each of the acoustic transceivers 10,000-frequencies within the plurality of frequencies;
emit, via the acoustic array, the cancellation signal;
receive, via the controller interface, a plurality of digital signals, the plurality of signals comprising:
a first 24-bit digital signal for each of the 10,000 frequencies from the DAC of each transceiver;
a second 24-bit signal for each of the 10,000 frequencies from the ADC of each transceiver; and
produce a high-resolution, three-dimensional signal with 84 bits of dynamic resolution from the plurality of digital signals by performing the following operations:
for each transceiver, combine the first 24-bit digital signal with the second 24-bit digital signal to produce a single-frequency transceiver signal having 48 bits of dynamic range per frequency per transceiver;

for each of the 10,000 frequencies, combine the single-frequency transceiver signal of each transceiver to produce a combined single-frequency signal having 68 bits of dynamic range per frequency;
combine each of the 10,000 single frequency signals to produce a multi-frequency signal having 81 bits of dynamic range; and
combine a plurality of multi-frequency signals received over a duration of eight seconds to produce the high-resolution, three-dimensional signal.

13. The apparatus of claim 12, wherein the instructions are further executable by the processor to:
determine the transmit focal point for the probe signal based on user input.

14. The apparatus of claim 12, wherein the instructions are further executable by the processor to:
provide a respective probe signal for each individual transmitter element of the first transceiver array, each probe signal having a respective phase delay based, at least in part, on the transmit focal point.

15. The apparatus of claim 12, wherein the instructions are further executable by the processor to:
determine a receive focal point of a captured signal;
provide, via the controller interface, the receive focal point for the captured signal to be obtained by the first transceiver array;
adjust, via the driver circuit, a second phase of the captured signal at one or more receiver elements of the first transceiver array based on the receive focal point; and
obtain, via the first transceiver array, the captured signal from the receive focal point.

16. The apparatus of claim 12, wherein the receive focal point and the transmit focal point are different points in three-dimensional space.

17. The apparatus of claim 12, wherein the instructions are further executable by the processor to:
determine the receive focal point for the probe signal based on user input.

18. The apparatus of claim 12, wherein the instructions are further executable by the processor to:
provide a respective phase delay for each respective captured signal from each individual receiver element of the first transceiver array, each captured signal having a respective phase delay based, at least in part, on the receive focal point.

19. A method comprising:
providing, via a controller interface, a probe signal to a driver circuit of an acoustic array having 1014 transceivers, the acoustic array comprising six array panels, each of the array panels including a respective transceiver array, each transceiver array comprising 169 transceivers, each transceiver comprising:
a transmitter element;
a receiver element;
a 24-bit digital to analog converter (DAC) to convert a digital signal to an analog signal for transmission by the transmitter element; and
a 24-bit analog to digital converter to convert an analog signal from the receiver element to a digital signal;
providing, via the controller interface, a cancellation signal to the driver input, to cancel incoming acoustic signals and correlated noise at each receiver element of the acoustic array;
providing, via the controller interface, a transmit focal point for the probe signal to be transmitted by the acoustic array;
adjusting, via the driver circuit, a first phase of the probe signal at one or more transmitter elements of the acoustic array based on the focal point; and
emitting, via the acoustic array, the probe signal at the focal point, wherein the probe signal is a broadband signal comprising a plurality of frequencies within a frequency band ranging from 10 Hz to 10 kHz, each of the acoustic transceivers transmitting 10,000 of the frequencies within the plurality of frequencies;
emitting, via the acoustic array, the cancellation signal;
receiving, via the controller interface, a plurality of digital signals, the plurality of signals comprising:
a first 24-bit digital signal for each of the 10,000 frequencies from the DAC of each transceiver;
a second 24-bit signal for each of the 10,000 frequencies from the ADC of each transceiver; and
producing a high-resolution, three-dimensional signal with 84 bits of dynamic resolution from the plurality of digital signals by performing the following operations:
for each transceiver, combining the first 24-bit digital signal with the second 24-bit digital signal to produce a single-frequency transceiver signal having 48 bits of dynamic range per frequency per transceiver;
for each of the 10,000 frequencies, combining the single-frequency transceiver signal of each transceiver to produce a combined single-frequency signal having 68 bits of dynamic range per frequency;
combining each of the 10,000 single frequency signals to produce a multi-frequency signal having 81 bits of dynamic range; and
combining a plurality of multi-frequency signals received over a duration of eight seconds to produce the three-dimensional, high-resolution signal.

20. The method of claim 19 further comprising:
determining a receive focal point of a captured signal;
providing, via the controller interface, the receive focal point for the captured signal to be obtained by the first transceiver array;
adjusting, via the driver circuit, a second phase of the captured signal at one or more receiver elements of the first transceiver array based on the receive focal point; and
obtaining, via the first transceiver array, the captured signal from the receive focal point.

21. The system of claim 1, wherein the system is configured to perform surface wave analysis for defects in one or more structures selected from a group consisting of roads and bridges.

* * * * *